United States Patent
Luo (10) Patent No.: US 11,434,419 B2
(45) Date of Patent: Sep. 6, 2022

(54) DEEP-RED LIGHT THERMALLY ACTIVATED DELAYED FLUORESCENT MATERIAL AND SYNTHESIZING METHOD THEREOF, AND ELECTROLUMINESCENT DEVICE

(71) Applicant: WUHAN CHINA STAR OPTOELECTRONICS SEMICONDUCTOR DISPLAY TECHNOLOGY CO., LTD., Wuhan (CN)

(72) Inventor: Jiajia Luo, Wuhan (CN)

(73) Assignee: WUHAN CHINA STAR OPTOELECTRONICS SEMICONDUCTOR DISPLAY TECHNOLOGY CO., LTD., Wuhan (CN)

( * ) Notice: Subject to any disclaimer, the term of this patent is extended or adjusted under 35 U.S.C. 154(b) by 551 days.

(21) Appl. No.: 16/462,138

(22) PCT Filed: Dec. 29, 2018

(86) PCT No.: PCT/CN2018/125432
§ 371 (c)(1),
(2) Date: May 17, 2019

(87) PCT Pub. No.: WO2020/082601
PCT Pub. Date: Apr. 30, 2020

(65) Prior Publication Data
US 2021/0332289 A1    Oct. 28, 2021

(30) Foreign Application Priority Data
Oct. 22, 2018 (CN) .......................... 201811226550.X (51) Int. Cl.
*C09K 11/06* (2006.01)
*H01L 51/00* (2006.01)
(Continued)

(52) U.S. Cl.
CPC ............ *C09K 11/06* (2013.01); *C07D 219/06* (2013.01); *C07D 265/38* (2013.01);
(Continued)

(58) Field of Classification Search
None
See application file for complete search history.

(56) References Cited

U.S. PATENT DOCUMENTS

2019/0027693 A1    1/2019   Zysman-Colman et al.
2020/0136048 A1    4/2020   Luo

FOREIGN PATENT DOCUMENTS

CN    106083824 A    11/2016
CN    108358908 A    8/2018
(Continued)

OTHER PUBLICATIONS

CN-105418533 machine translation from Google Patents, downloaded, Sep. 11, 2021.*

*Primary Examiner* — Clinton A Brooks
(74) *Attorney, Agent, or Firm* — Osha Bergman Watanabe & Burton LLP (57) ABSTRACT

A deep-red light thermally activated delayed fluorescent material and a synthesizing method thereof, and an electroluminescent device are described. The deep-red light thermally activated delayed fluorescent material is a target compound reacted and synthesized by an electron donor and an electron acceptor. The target compound is a D-A molecular structure or a D-A-D molecular structure, wherein the electron acceptor is a planar electron acceptor with an ultra-low triplet state energy level, and a triplet state energy
(Continued)

level of the target compound ranges from 1.0 to 2.0 eV. The synthesized deep-red light thermally activated delayed fluorescent material provides high electroluminescent performance, the synthesis efficiency thereof is improved, and the preparation of the highly efficient organic electroluminescent device is realized.

3 Claims, 2 Drawing Sheets

(51) Int. Cl.
   *C07D 219/06* (2006.01)
   *C07D 265/38* (2006.01)
   *C07D 279/26* (2006.01)
   *H01L 51/50* (2006.01)
   *H01L 51/56* (2006.01)

(52) U.S. Cl.
   CPC ........ *C07D 279/26* (2013.01); *H01L 51/0071* (2013.01); *H01L 51/0072* (2013.01); *C09K 2211/1011* (2013.01); *C09K 2211/1018* (2013.01); *H01L 51/0003* (2013.01); *H01L 51/0025* (2013.01); *H01L 51/5016* (2013.01); *H01L 51/56* (2013.01)

(56) References Cited

FOREIGN PATENT DOCUMENTS

| CN | 109467681 A | 3/2019 |
|---|---|---|
| WO | 2017115068 A1 | 7/2017 |

* cited by examiner

DEEP-RED LIGHT THERMALLY ACTIVATED DELAYED FLUORESCENT MATERIAL AND SYNTHESIZING METHOD THEREOF, AND ELECTROLUMINESCENT DEVICE

FIELD OF DISCLOSURE

The present disclosure relates to displays, and more particularly to a deep-red light thermally activated delayed fluorescent material and a synthesizing method thereof, and an electroluminescent device.

BACKGROUND OF DISCLOSURE

Organic electroluminescence is a kind of luminescence phenomenon that is realized by an excitation of an organic material under an applied electric field and current. In fact, as early as 1963, Pope et al. of a university of New York in the United States first observed the organic electroluminescence phenomenon with a single crystal germanium as the light-emitting layer at a driving voltage of 100 V. However, due to low luminous efficiency, high driving voltage, and other defects, widespread attention was not received, and research on organic light emitting diode (OLED) display technology was temporarily stagnated. Until 1987, C. W. Tang et al. of Kodak Company of the United States adopted vacuum evaporation technology, using aromatic diamine as a hole transporting layer, and 8-hydroxyquinoline aluminum (Alq3) as a new type of an electron transporting layer and a luminescent layer. The layered OLED display device achieved higher brightness (1000 cd/m$^2$), higher external quantum efficiency (>1%), and lower driving voltage (~10 V), which inspired researchers to study the OLED. Great interest has also made it possible to commercialize it. Since then, in 1990, Friend et al. of the University of Cambridge in the United Kingdom prepared a polymer electroluminescent device (PLED) based on styrene conjugated polymer (PPV) as a luminescent material, opening up a new direction for a development of the OLED. Subsequently, Heeger et al. prepared a fully flexible PLED with a flexible plastic as a substrate, fully demonstrating the charm of the fantastic display of the OLED display device. In 1998, Forrest et al. of Princeton University used a "heavy atom effect" to realize the phosphorescence emission at room temperature for the first time using triplet state excitons. The phosphorescent photoluminescence device (PhOLED) prepared based on this actually surpassed a theoretical limit of an internal quantum efficiency of OLED which is not more than 25%. In 2012, Adachi et al. of Kyushu University in Japan reported an OLED device with a delayed quantum phenomenon with an external quantum efficiency of more than 5% and an internal quantum efficiency of more than 25%, which utilized the triplet state excitons to form singlet excitons after absorbing heat energy to achieve fluorescence emission, which had characteristics of thermally activated delayed fluorescence (TADF). The advent and development of TADF technology have greatly broadened the concept of research on OLED display technology, which has allowed research on OLED display technology to enter a booming era.

For thermally activated delayed fluorescent materials, a fast reverse intersystem crossing constant (kRISC) and high photoluminescence quantum yield (PLQY) are necessary for the preparation of highly efficient OLED display devices. At present, the thermally activated delayed fluorescent material having the above conditions is relatively scarce comparing with a heavy metal Ir complex, and in the deep-red light field in which a breakthrough in the phosphorescent heavy metal material is to be made, there are few heat activated delayed fluorescent materials.

SUMMARY OF DISCLOSURE

In a thermally activated delayed fluorescent material system in the prior art, technical problems are that a photoluminescence quantum yield is low, and a proportion of the thermally activated delayed fluorescent material in an entire thermal activated delayed fluorescent material system is low.

The present disclosure provides a deep-red light thermally activated delayed fluorescent material, which is a target compound reacted and synthesized by an electron donor and an electron acceptor, wherein the target compound is a D-A molecular structure or a D-A-D molecular structure, the D in the molecular structure is the electron donor, the A is the electron acceptor, the electron acceptor is a planar electron acceptor with an ultra-low triplet state energy level, and a triplet state energy level of the target compound ranges from 1.0 to 2.0 eV.

Further, the electron acceptor is 4,8-dibromo-2,3,6,7,-tetracyanonaphthalene, and the electron donor includes at least one of phenoxazine, phenothiazine, and 3,6-dimethoxy-9,9-dimethyl acridine.

Further, the D-A molecular structure of the deep-red light thermally activated delayed fluorescent material is:

or wherein the D-A-D molecular structure of the deep-red light thermally activated delayed fluorescent material is:

The present disclosure further provides a synthesizing method of a deep-red light thermally activated delayed fluorescent material, comprising following steps of: a reaction solution preparation step of placing an electron donor, an electron acceptor, and a catalyst into a reaction vessel to obtain a reaction solution; a target compound synthesis step of placing the reaction solution at a temperature from 100° C. to 200° C. to thoroughly react and thus obtain a mixed solution, wherein the mixed solution has a target compound formed after reacting; an extraction step of cooling the mixed solution to a room temperature to extract the target compound from the mixed solution; and a target compound purification treatment step of separating and purifying the target compound to obtain the deep-red light thermally activated delayed fluorescent material.

Further, the reaction solution preparation step further comprises an electron acceptor preparation step including: a mixed solution preparation step of adding 2,3,6,7,-tetracyanonaphthalene into a two-necked flask and then adding toluene, and dropping liquid bromine into the two-necked flask at room temperature and thoroughly stirring and reacting to obtain a mixed solution; a filtration step of cooling the first reaction solution to room temperature, adding an ice-water mixture, and filtering the mixed solution to obtain a gray-red solid; a gray-red solid purification treatment step of dissolving the gray-red solid in dichloromethane, and initially purifying the target compound by a silica gel column chromatography to obtain an initial purified product; and further purifying the initial purified product using a recrystallization method to obtain the electron acceptor.

Further, the electron acceptor is selected from 4,8-dibromo-2,3,6,7,-tetracyanonaphthalene; wherein the electron donor is selected from at least one of phenoxazine, phenothiazine, and 3,6-dimethoxy-9,9-dimethyl acridine; and wherein the catalyst includes palladium acetate, tri-tert-butylphosphine tetrafluoroborate, and sodium t-butoxide.

Further, in the reaction solution preparation step, a molar ratio of the electron acceptor to the electron donor is from 1:1 to 1:3.

Further, in the reaction solution preparation step, the palladium acetate and the tri-tert-butylphosphine tetrafluoroborate together with the electron acceptor and the electron donor are placed into the reaction vessel, the reaction vessel is further placed under an argon gas environment, and the sodium t-butoxide and toluene which removes water and oxygen are added into the reaction vessel, so as to obtain the reaction solution.

Further, the extraction step comprises: pouring the reaction solution into an ice water mixture, and performing multiple extractions using dichloromethane; and after the multiple extractions, combining organic phases to obtain the target compound; and wherein a step of purifying the target compound comprises: initially purifying the target compound by a silica gel column chromatography using a developing solvent to obtain an initial purified product; and further purifying the initial purified material by a recrystallization method to obtain the deep-red light thermally activated delayed fluorescent material; and wherein the developing agent in the silica gel column chromatography method is dichloromethane and n-hexane, and a volume ratio of the dichloromethane to the n-hexane is 1:1.

The present disclosure further provides an electroluminescent device comprising: a substrate layer; a hole transporting and injecting layer disposed on a side surface of the substrate layer; a luminescent layer disposed on a side surface of the hole transporting and injecting layer away from the substrate layer; an electron transporting layer disposed on a side surface of the luminescent layer away from the hole transporting and injecting layer; and a cathode layer disposed on a side surface of the electron transporting layer away from the luminescent; wherein a material of the luminescent layer is a deep-red light thermally activated delayed fluorescent material.

A technical effect of the present disclosure is that a deep-red light thermally activated delayed fluorescent material of the disclosure reduces a lowest singlet-triplet state energy level difference of a target molecule and a near-infrared light emission through a clever molecular design, so that the target molecule has a fast reverse intersystem crossing constant (the constant value ranges from $1\times10^4$/s to $1\times10^7$/s).

A synthesizing method of the deep-red light thermally activated delayed fluorescent material of the disclosure synthesizes a series of deep-red light thermally activated delayed fluorescent materials with remarkable thermal activation delayed fluorescence characteristics through different coordination of functional groups, which has a high synthesis percentage. Among the synthesizing products, the thermally activated delayed fluorescent material has a high proportion in the entire synthesized products, and its photoluminescence quantum yield is high. Further, an organic electroluminescent device is improved such that the organic electroluminescent device with the deep-red light thermally activated delayed fluorescent material has a relatively high luminous efficiency and a relatively high brightness.

Some components are identified as follows:
1: substrate layer;
2: hole transporting and injecting layer;
3: luminescent layer;
4: electron transporting layer; and
5: cathode layer.

DETAILED DESCRIPTION OF PREFERRED EMBODIMENTS

Preferred embodiments of the present disclosure are described in detail below with reference to the accompanying drawings in order to explain technical details of the present disclosure to those skilled in the art so as to exemplify the disclosure. Those skilled in the art will more readily understand how to implement the disclosure. The present disclosure, however, may be embodied in many different forms of embodiments, and the scope of the present disclosure is not limited to the embodiments described herein. The description of the embodiments below is not intended to limit the scope of the disclosure.

The directional terms described by the present disclosure, such as "upper", "lower", "front", "back", "left", "right", "inner", "outer", "side", etc. are only directions by referring to the accompanying drawings. Thus, the used directional terms are used to describe and understand the present disclosure, but the scope of the present disclosure is not limited thereto.

In figures, elements with similar structures are indicated with the same numbers. Components that are structurally or functionally similar are denoted by similar reference numerals. Moreover, size and thickness of each component shown in the drawings are arbitrarily shown for ease of understanding and description, and the disclosure does not limit the size and thickness of each component.

When some components are described as "on" another component, the components may be placed directly on the another component; or may also be an intermediate component in which the component is placed on the intermediate component, and the intermediate component is placed on the another component.

Embodiment 1

The present embodiment provides a deep-red light thermally activated delayed fluorescent material, which is a target compound reacted and synthesized by an electron donor and an electron acceptor, wherein the target compound is a D-A molecular structure or a D-A-D molecular structure. In the molecular structure, the D is the electron donor, the A is the electron acceptor. The electron acceptor is a planar electron acceptor with an ultra-low triplet state energy level, and a triplet state energy level of the target compound ranges from 1.0 to 2.0 eV. In the present embodiment, the electron acceptor is 4,8-dibromo-2,3,6,7,-tetracyanonaphthalene, and the electron donor is phenoxazine. The phenoxazine has a molecular formula of $C_{12}H_9NO$, and the 4,8-dibromo-2,3,6,7,-tetracyanophthalene and the phenoxazine is synthesized by a series of chemical reactions to synthesize a first target compound. A molecular structure of the first target compound is as follows:

A lowest singlet-triplet state energy level difference of a target molecule and a near-infrared light emission are reduced through a clever molecular design, so that the target molecule has a fast reverse intersystem crossing constant (the constant value ranges from $1 \times 10^4$/s to $1 \times 10^7$/s) and a high photoluminescence quantum yield. The synthesized first target compound has a high thermally activated delayed fluorescence (TADF) ratio and photoluminescence quantum yield (PLQY).

Figure 1:
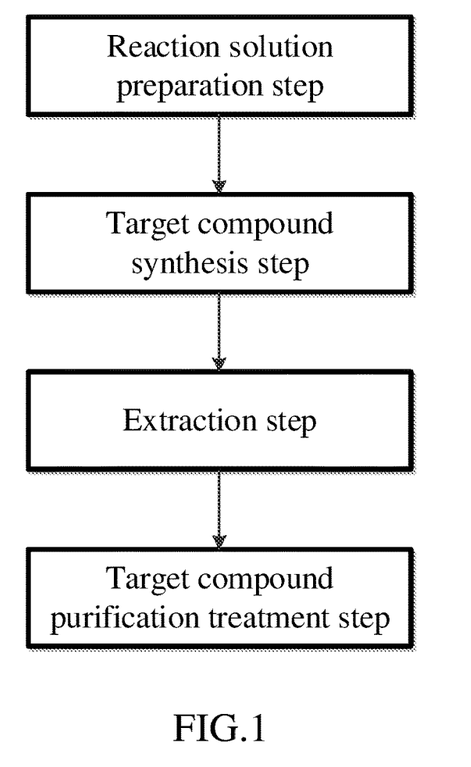
FIG. 1 is a flowchart of a synthesizing method of a deep-red light thermally activated delayed fluorescent material according to an embodiment of the present disclosure.
Figure 2:
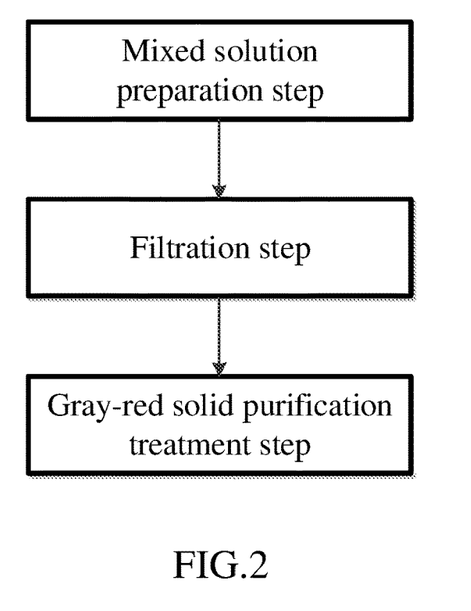
FIG. 2 is a flowchart of steps of preparing an electron acceptor according to an embodiment of the present disclosure.

As shown in FIG. 1, the present embodiment further provides a synthesizing method for a deep-red light thermally activated delayed fluorescent material of the disclosure, and a synthetic route is shown as follows:

-continued

A specific step includes an electron acceptor preparation step. The electron acceptor preparation step includes a reaction solution preparation step of preparing a 200 mL to 300 mL two-necked flask, and 8 mmol to 12 mmol of 2,3,6,7-tetracyanonaphthalene, 60 mL to 100 mL of toluene, and 35 mmol to 40 mmol of liquid bromine. In this example, 2.28 g of 10 mmol of the 2,3,6,7-tetracyanonaphthalene is added into a 250 mL two-necked flask. Then, 80 mL of the toluene is added, and 2 mL of 39 mmol of the liquid bromine is dropped into the two-necked flask at room temperature, and the reaction was performed by thoroughly stirring at room temperature to obtain a mixed solution.

In a filtration step, the first reaction solution is cooled to room temperature, the mixed solution is poured into a 200 mL suction bottle containing an ice water mixture, and the mixed solution is filtered by an air pump to reduce pressure in the suction bottle so that the mixed solution is filtered in the suction flask to obtain a gray-red solid.

In an electron acceptor purification processing step, the gray-red solid is dissolved in dichloromethane, and the target compound is initially purified by a silica gel column chromatography to obtain an initial purified product. In the silica gel column chromatography method, a volume ratio of the dichloromethane to the toluene is 3:1. Further, the initial purified product is purified by a recrystallization method to obtain the electron acceptor, which is 2.38 g of 4,8-dibromo-2,3,6,7-tetracyanophthalene and has a yield of 62%.

Results of a nuclear magnetic resonance spectrum and a carbon spectrum are $^1$H NMR (300 MHz, $CD_2Cl_2$, δ): 8.93 (s, 2H).

A result of mass spectral is: MS (El) m/z: $[M]^+$ calcd (theoretical value) for $C_{14}H_2BrN_4$, 383.86; found (experimental value), 383.67.

A result of elemental analysis is: Anal. Calcd (theoretical value) for $C_{14}H_2BrN_4$: C 43.56, H 0.52, and N 14.51; found (experimental value): C 43.66, H 0.63, and N 14.35.

In a reaction solution preparation step, a 50 mL-200 mL two-necked bottle, 0-10 mmol electron acceptor of 4,8-dibromo-2,3,6,7-tetracyanonaphthalene, 10 mmol -15 mmol electron donor of phenoxazine, 0-1 mmol palladium acetate, 1 mmol -2 mmol tri-tert-butylphosphine tetrafluoroborate, and 10 mmol -15 mmol sodium t-butoxide (NaOt-Bu). A molar ratio of the electron acceptor to the electron donor is 1:1 to 1:3.

In the present embodiment, 1.92 g (5 mmol) of the electron acceptor 4,8-dibromo-2,3,6,7-tetracyanonaphthalene, 2.2 g (12 mmol) of the electron donor of phenoxazine, a catalyst of 90 mg (0.4 mmol) of palladium acetate, and 0.34 g (1.2 mmol) of tri-tert-butylphosphine tetrafluoroborate are placed in a 100 mL two-necked flask, and 1.16 g (12 mmol) of sodium t-butoxide (NaOt-Bu) is added into the 100 mL two-necked flask in a glove box, the reaction liquid is obtained. Because sodium t-butoxide (NaOt-Bu) reacts easily with water to release hydrogen, it is very dangerous. Therefore, it is stored in the glove box under an argon atmosphere, and it is also used under the argon atmosphere.

In a target compound synthesis step, reaction conditions of the reaction solution are provided. 30 mL to 50 mL of water and deoxygenated toluene are added into the glove box to thoroughly react at a temperature of 100° C. to 200° C. to obtain a mixed solution. The mixed solution has a target compound formed by the reaction.

In an extraction step, the mixed solution is cooled to a room temperature and poured into a 30 mL to 80 mL ice-water mixture. The target compound in the mixed solution is extracted multiple times with the dichloromethane to extract the target compound from the mixed solution.

In a target compound purification treatment step, an organic phase is combined, and the target compound is initially purified by silica gel column chromatography using a developing solvent to obtain a primary purified product. In the silica gel column chromatography method, a volume ratio of the dichloromethane to n-hexane is 1:1. The n-hexane is the solvent in the column chromatography step, and the target compound is isolated and purified to obtain a deep red powder of 1.47 g in a yield of 50%, and the deep red powder is further purified by a recrystallization method to obtain 1.1 g of the first target compound.

Results of a nuclear magnetic resonance spectrum and a carbon spectrum are $^1$H NMR (300 MHz, $CD_2Cl_2$, δ): 9.34 (s, 2H), 7.14-7.06 (m, 4H), 7.01-7.96 (m, 12H).

A result of mass spectral is: MS (El) m/z: $[M]^+$ calcd for $C_{38}H_{18}N_6O_2$, 590.12; found, 590.07.

A result of elemental analysis is: Anal. Calcd for $C_{38}H_{18}N_6O_2$: C 77.28, H 3.07, and N 14.23; found: C 77.17, H 2.93, and N 14.02.

The deep-red light thermally activated delayed fluorescent material reduces a lowest singlet-triplet state energy level difference of a target molecule and a near-infrared light emission through a clever molecular design, so that the target molecule has a fast reverse intersystem crossing constant (the constant value ranges from $1\times10^4$/s to $1\times10^7$/s). The synthesizing method of the deep-red light thermally activated delayed fluorescent material synthesizes a series of deep-red light thermally activated delayed fluorescent materials with remarkable thermal activation delayed fluorescence characteristics through different coordination of functional groups, which has a high synthesis percentage. Among the synthesizing products, the thermally activated delayed fluorescent material has a high proportion in the entire synthesized products, and its photoluminescence quantum yield is high.

Characteristic parameters of a first target compound are shown in Table 1 below.

Table 1 shows the measured parameters such as the lowest singlet state (S1) and the lowest triplet state energy level (T1) of the first target compound:

| Compound | PL Peak (nm) | $S_1$ (eV) | $T_1$ (eV) | $\Delta E_{ST}$ (eV) | HOMO (eV) | LUMO (eV) |
|---|---|---|---|---|---|---|
| First target compound | 650 | 1.91 | 1.74 | 0.17 | −5.40 | −3.58 |

Figure 3:
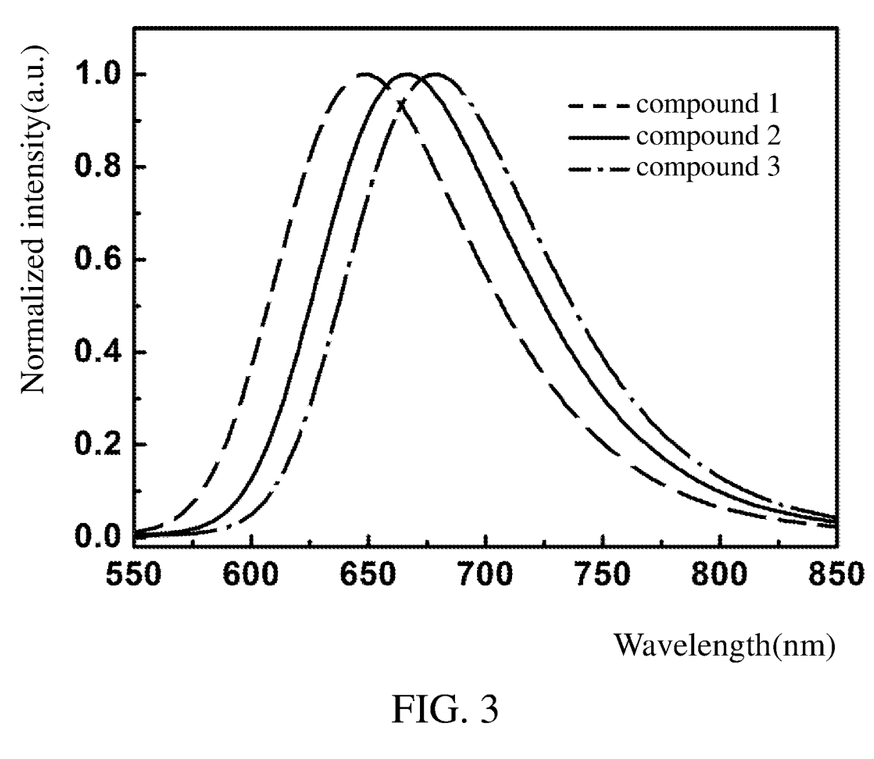
FIG. 3 is a photoluminescence spectrum of a synthesized compound according to an embodiment of the present disclosure in a toluene solution at room temperature.

A photoluminescence spectrum of the first target compound in a toluene solution at room temperature is shown in FIG. 3.

Figure 4:
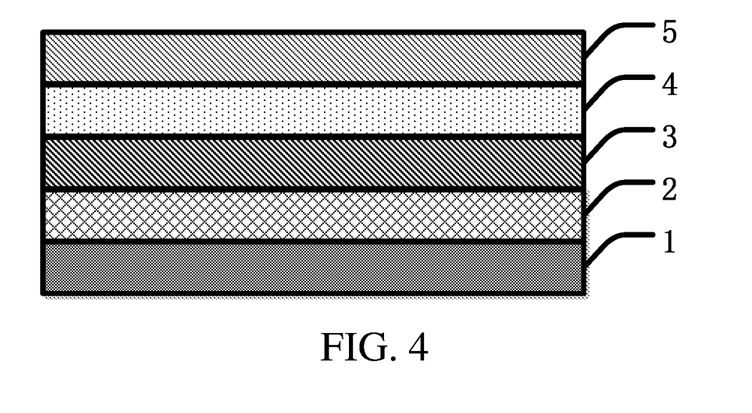
FIG. 4 is a structural schematic diagram of an electroluminescent device according to an embodiment of the present disclosure.

As shown in FIG. 4, the present embodiment further provides an electroluminescent device comprising a substrate layer 1; a hole transporting and injecting layer 2 disposed on an upper surface of the substrate layer 1; a luminescent layer 3 disposed on an upper surface of the hole transporting and injecting layer 2; an electron transporting layer 4 disposed on an upper surface of the luminescent layer 3; and a cathode layer 5 disposed on an upper surface of the electron transporting layer 4, wherein a material of the luminescent layer 3 is a deep-red light thermally activated delayed fluorescent material, i.e., the first target compound.

A 50 nm poly 3,4-ethylenedioxythiophene: polystyrene sulfonate (PEDOT:PSS) is spin-coated on a cleaned substrate layer 1 to obtain a hole transporting and injecting layer 2. A material of the substrate layer 1 is glass and conductive glass (ITO). A 40 nm deep-red light thermally activated delayed material is spin-coated on the hole transporting and injecting layer 2 to obtain a luminescent layer 3. A layer of 40 nm of 1,3,5-tris(3-(3-pyridyl)phenyl)benzene (Tm3PyPB) is evaporated on the luminescent layer 3 under high vacuum to obtain an electron transporting layer 4. Further, under high vacuum conditions, a layer of 1 nm lithium fluoride and 100 nm aluminum are evaporated on the electron transporting layer 4 to obtain a cathode layer 5, thereby finally forming a first electroluminescent device.

A current-brightness-voltage characteristic of the device is performed by a Keithley source measurement system (Keithley 2400 Sourcemeter, Keithley 2000 Currentmeter) with a calibrated silicon photodiode. An electroluminescence spectrum is measured by a French JY company SPEX CCD3000 spectrometer. All measurements are done at room temperature in an atmosphere.

A performance data of the first electroluminescent device is shown in Table 2 below.

Table 2 shows measured parameters such as a highest brightness and a highest current efficiency of the first electroluminescent device:

| Electroluminescent device | highest brightness (cd/m$^2$) | highest current efficiency (cd/A) | CIEx | Maximum external quantum efficiency (%) |
|---|---|---|---|---|
| First electroluminescent device | 8630 | 23.6 | 0.66 | 13.2 |

The electroluminescent device fabricated by deep-red light thermally activated delayed fluorescent material has a relatively high luminous efficiency and brightness, a high production efficiency, and a long service life.

When a molar ratio of the electron acceptor to the electron donor is from 1:1 to 1:5, the synthesized molecular structure is a D-A molecular structure. The molecular structure is as follows:

The thermally activated delayed fluorescent material of the D-A molecular structure has a high proportion in the entire synthesized product, and its photoluminescence quantum yield is high but the performance is lower than a D-A-D structure. The D-A-D structure reduces the lowest singlet-triplet energy level difference of the target molecule and a near-infrared light emission, so that the target molecule has a fast reverse intersystem crossing constant (the constant value ranges from $1\times10^4$/s to $1\times10^7$/s) and a high photoluminescence quantum yield.

Embodiments of the Present Disclosure

Embodiment 2

The present embodiment provides a deep-red light thermally activated delayed fluorescent material, which is a target compound reacted and synthesized by an electron donor and an electron acceptor, wherein the target compound is a D-A molecular structure or a D-A-D molecular structure. In the molecular structure, the D is the electron donor, the A is the electron acceptor. The electron acceptor is a planar electron acceptor with an ultra-low triplet state energy level, and a triplet state energy level of the target compound ranges from 1.0 to 2.0 eV. In the present embodiment, the electron acceptor is 4,8-dibromo-2,3,6,7,-tetracyanonaphthalene, and the electron donor is phenothiazine. The phenothiazine has a molecular formula of $C_{12}H_9NS$, and the 4,8-dibromo-2,3,6,7,-tetracyanophthalene and the phenothiazine is synthesized by a series of chemical reactions to synthesize a second target compound. A molecular structure of a second target compound is as follows:

A lowest singlet-triplet state energy level difference of a target molecule and a near-infrared light emission are reduced through a clever molecular design, so that the target molecule has a fast reverse intersystem crossing constant (the constant value ranges from $1\times10^4$/s to $1\times10^7$/s) and a high photoluminescence quantum yield. The synthesized second target compound has a high TADF ratio and PLQY.

As shown in FIG. 1, the present embodiment further provides a synthesizing method for a deep-red light thermally activated delayed fluorescent material of the disclosure, and a synthetic route is shown as follows:

A specific step including an electron acceptor preparation step. The electron acceptor preparation step includes a reaction solution preparation step of preparing a 200 mL to 300 mL two-necked flask, and 8 mmol to 12 mmol of 2,3,6,7-tetracyanonaphthalene, 60 mL to 100 mL of toluene, and 35 mmol to 40 mmol of liquid bromine. In this example, 2.28 g of 10 mmol of the 2,3,6,7-tetracyanonaphthalene is added into a 250 mL two-necked flask. Then, 80 mL of the toluene is added, and 2 mL of 39 mmol of the liquid bromine is dropped into the two-necked flask at room temperature, and the reaction was performed by thoroughly stirring at room temperature to obtain a mixed solution.

In a filtration step, the first reaction solution is cooled to room temperature, the mixed solution is poured into a 200 mL suction bottle containing an ice water mixture, and the mixed solution is filtered by an air pump to reduce pressure in the suction bottle so that the mixed solution is filtered in the suction flask to obtain a gray-red solid.

In an electron acceptor purification processing step, the gray-red solid is dissolved in dichloromethane, and the target compound is initially purified by a silica gel column chromatography to obtain an initial purified product. In the silica gel column chromatography method, a volume ratio of the dichloromethane to the toluene is 3:1. Further, the initial purified product is purified by a recrystallization method to obtain the electron acceptor, which is 2.38 g of 4,8-dibromo-2,3,6,7-tetracyanophthalene and has a yield of 62%.

Results of a nuclear magnetic resonance spectrum and a carbon spectrum are $^1$H NMR (300 MHz, $CD_2Cl_2$, δ): 8.93 (s, 2H).

A result of mass spectral is: MS (EI) m/z: $[M]^+$ calcd (theoretical value) for $C_{14}H_2BrN_4$, 383.86; found (experimental value), 383.67.

A result of elemental analysis is: Anal. Calcd (theoretical value) for $C_{14}H_2BrN_4$: C 43.56, H 0.52, and N 14.51; found (experimental value): C 43.66, H 0.63, and N 14.35.

In a reaction solution preparation step, a 50 mL-200 mL two-necked bottle, 0-10 mmol electron acceptor of 4,8-dibromo-2,3,6,7-tetracyanonaphthalene, 10 mmol -15 mmol electron donor of phenothiazine, 0-1 mmol palladium acetate, 1 mmol-2 mmol tri-tert-butylphosphine tetrafluoroborate, and 10 mmol-15 mmol sodium t-butoxide (NaOt-Bu). A molar ratio of the electron acceptor to the electron donor is 1:1 to 1:2.5.

In the present embodiment, 1.92 g (5 mmol) of the electron acceptor 4,8-dibromo-2,3,6,7-tetracyanonaphthalene, 2.2 g (10 mmol) of the electron donor of phenothiazine, a catalyst of 90 mg (0.4 mmol) of palladium acetate, and 0.34 g (1.2 mmol) of tri-tert-butylphosphine tetrafluoroborate are placed in a 100 mL two-necked flask, and 1.16 g (12 mmol) of sodium t-butoxide (NaOt-Bu) is added into the a 100 mL two-necked flask in a glove box, the reaction liquid is obtained. Because sodium t-butoxide (NaOt-Bu) reacts easily with water to release hydrogen, it is very dangerous. Therefore, it is stored in the glove box under an argon atmosphere, and it is also used under the argon atmosphere.

In a target compound synthesis step, reaction conditions of the reaction solution are provided. 30 mL to 50 mL of water and deoxygenated toluene are added into the glove box to thoroughly react at a temperature of 100° C. to 200° C. to obtain a mixed solution. The mixed solution has a target compound formed by the reaction.

In an extraction step, the mixed solution is cooled to a room temperature and poured into a 30 mL to 80 mL ice-water mixture. The target compound in the mixed solution is extracted multiple times with the dichloromethane to extract the target compound from the mixed solution.

In a target compound purification treatment step, an organic phase is combined, and the target compound is initially purified by silica gel column chromatography using a developing solvent to obtain a primary purified product. In the silica gel column chromatography method, a volume ratio of the dichloromethane to n-hexane is 1:1. The n-hexane is the solvent in the column chromatography step, and the target compound is isolated and purified to obtain a deep red powder of 1.34 g in a yield of 43%, and the deep red powder is further purified by a recrystallization method to obtain 0.88 g of the second target compound.

Results of a nuclear magnetic resonance spectrum and a carbon spectrum are: $^1$H NMR (300 MHz, $CD_2Cl_2$, δ): 8.314 (s, 2H), 7.21-7.16 (m, 12H), 6.97-6.91 (m, 4H).

A result of mass spectral is: MS (EI) m/z: $[M]^+$ calcd for $C_{38}H_{18}N_6S_2$, 622.10; found, 622.07.

A result of elemental analysis is: Anal. Calcd for $C_{38}H_{18}N_6S_2$: C 73.29, H 2.91, and N 13.50; found: C 73.19, H 2.93, and N 13.32.

The deep-red light thermally activated delayed fluorescent material reduces a lowest singlet-triplet state energy level difference of a target molecule and a near-infrared light emission through a clever molecular design, so that the target molecule has a fast reverse intersystem crossing constant (the constant value ranges from $1 \times 10^4$/s to $1 \times 10^7$/s). The synthesizing method of the deep-red light thermally activated delayed fluorescent material synthesizes a series of deep-red light thermally activated delayed fluorescent materials with remarkable thermal activation delayed fluorescence characteristics through different coordination of functional groups, which has a high synthesis percentage. Among the synthesizing products, the thermally activated delayed fluorescent material has a high proportion in the entire synthesized products, and its photoluminescence quantum yield is high.

Characteristic parameters of the second target compound are shown in Table 3 below.

Table 3 shows the measured parameters such as the lowest singlet state (S1) and the lowest triplet state energy level (T1) of the second target compound:

| Compound | PL Peak (nm) | $S_1$ (eV) | $T_1$ (eV) | $\Delta E_{ST}$ (eV) | HOMO (eV) | LUMO (eV) |
| --- | --- | --- | --- | --- | --- | --- |
| Second target compound | 668 | 1.86 | 1.60 | 0.26 | −5.72 | −3.42 |

A photoluminescence spectrum of the second target compound in a toluene solution at room temperature is shown in FIG. 3.

As shown in FIG. 4, the present embodiment further provides an electroluminescent device comprising a substrate layer 1; a hole transporting and injecting layer 2 disposed on an upper surface of the substrate layer 1; a luminescent layer 3 disposed on an upper surface of the hole transporting and injecting layer 2; an electron transporting layer 4 disposed on an upper surface of the luminescent layer 3; and a cathode layer 5 disposed on an upper surface of the electron transporting layer 4, wherein a material of the luminescent layer 3 is a deep-red light thermally activated delayed fluorescent material, i.e., the second target compound.

A 50 nm poly 3,4-ethylenedioxythiophene: polystyrene sulfonate (PEDOT:PSS) is spin-coated on a cleaned substrate layer 1 to obtain a hole transporting and injecting layer 2. A material of the substrate layer 1 is glass and conductive glass (ITO). A 40 nm deep-red light thermally activated delayed material is spin-coated on the hole transporting and injecting layer 2 to obtain a luminescent layer 3. A layer of 40 nm of 1,3,5-tris(3-(3-pyridyl)phenyl)benzene (Tm3PyPB) is evaporated on the luminescent layer 3 under high vacuum to obtain an electron transporting layer 4. Further, under high vacuum conditions, a layer of 1 nm lithium fluoride and 100 nm aluminum are evaporated on the electron transporting layer 4 to obtain a cathode layer 5, thereby finally forming a first electroluminescent device.

A current-brightness-voltage characteristic of the device is performed by a Keithley source measurement system (Keithley 2400 Sourcemeter, Keithley 2000 Currentmeter) with a calibrated silicon photodiode. An electroluminescence spectrum is measured by a French JY company SPEX CCD3000 spectrometer. All measurements are done at room temperature in an atmosphere.

A performance data of the second electroluminescent device is shown in Table 4 below.

Table 4 shows measured parameters such as a highest brightness and a highest current efficiency of the second electroluminescent device:

| Electroluminescent device | highest brightness (cd/m²) | highest current efficiency (cd/A) | CIEx | Maximum external quantum efficiency (%) |
| --- | --- | --- | --- | --- |
| Second electroluminescent device | 5789 | 28.9 | 0.68 | 14.7 |

The electroluminescent device fabricated by deep-red light thermally activated delayed fluorescent material has a relatively high luminous efficiency and brightness, a high production efficiency and a long service life.

When a molar ratio of the electron acceptor to the electron donor is from 1:1 to 1:3, the synthesized molecular structure is a D-A molecular structure. The molecular structure is as follows:

The thermally activated delayed fluorescent material of the D-A molecular structure has a high proportion in the entire synthesized product, and its photoluminescence quantum yield is high but the performance is lower than a D-A-D structure. The D-A-D structure reduces the lowest singlet-triplet energy level difference of the target molecule and a near-infrared light emission, so that the target molecule has a fast reverse intersystem crossing constant (the constant value ranges from 1×10⁴/s to 1×10⁷/s) and a high photoluminescence quantum yield.

Embodiment 3

The present embodiment provides a deep-red light thermally activated delayed fluorescent material, which is a target compound reacted and synthesized by an electron donor and an electron acceptor, wherein the target compound is a D-A molecular structure or a D-A-D molecular structure. In the molecular structure, the D is the electron donor, the A is the electron acceptor. The electron acceptor is a planar electron acceptor with an ultra-low triplet state energy level, and a triplet state energy level of the target compound ranges from 1.0 to 2.0 eV. In the present embodiment, the electron acceptor is 4,8-dibromo-2,3,6,7,-tetracyanonaphthalene, and the electron donor is 3,6-dimethoxy-9,9-dimethyl acridine. The 4,8-dibromo-2,3,6,7,-tetracyanophthalene and the 3,6-dimethoxy-9,9-dimethyl acridine is synthesized by a series of chemical reactions to synthesize a second target compound. A molecular structure of the third target compound is as follows:

A lowest singlet-triplet state energy level difference of a target molecule and a near-infrared light emission are reduced through a clever molecular design, so that the target molecule has a fast reverse intersystem crossing constant (the constant value ranges from $1\times10^4$/s to $1\times10^7$/s) and a high photoluminescence quantum yield. The synthesized second target compound has a high TADF ratio and PLQY.

As shown in FIG. 1, the present embodiment further provides a synthesizing method for a deep-red light thermally activated delayed fluorescent material of the disclosure, and a synthetic route is shown as follows:

A specific step include an electron acceptor preparation step. The electron acceptor preparation step includes: a reaction solution preparation step of preparing a 200 mL to 300 mL two-necked flask, and 8 mmol to 12 mmol of 2,3,6,7-tetracyanonaphthalene, 60 mL to 100 mL of toluene, and 35 mmol to 40 mmol of liquid bromine. In this example, 2.28 g of 10 mmol of the 2,3,6,7-tetracyanonaphthalene is added into a 250 mL two-necked flask. Then, 80 mL of the toluene is added, and 2 mL of 39 mmol of the liquid bromine is dropped into the two-necked flask at room temperature, and the reaction was performed by thoroughly stirring at room temperature to obtain a mixed solution.

In a filtration step, the first reaction solution is cooled to room temperature, the mixed solution is poured into a 200 mL suction bottle containing an ice water mixture, and the mixed solution is filtered by an air pump to reduce pressure in the suction bottle so that the mixed solution is filtered in the suction flask to obtain a gray-red solid.

In an electron acceptor purification processing step, the gray-red solid is dissolved in dichloromethane, and the target compound is initially purified by a silica gel column chromatography to obtain an initial purified product. In the silica gel column chromatography method, a volume ratio of the dichloromethane to the toluene is 3:1. Further, the initial purified product is purified by a recrystallization method to obtain the electron acceptor, which is 2.38 g of 4,8-dibromo-2,3,6,7-tetracyanophthalene and has a yield of 62%.

Results of a nuclear magnetic resonance spectrum and a carbon spectrum are: $^1$H NMR (300 MHz, $CD_2Cl_2$, δ): 8.93 (s, 2H).

A result of mass spectral is: MS (El) m/z: $[M]^+$ calcd (theoretical value) for $C_{14}H_2BrN_4$, 383.86; found (experimental value), 383.67.

A result of elemental analysis is: Anal. Calcd (theoretical value) for $C_{14}H_2BrN_4$: C 43.56, H 0.52, and N 14.51; found (experimental value): C 43.66, H 0.63, and N 14.35.

In a reaction solution preparation step, a 50 mL-200 mL two-necked bottle, 0-10 mmol electron acceptor of 4,8-dibromo-2,3,6,7-tetracyanonaphthalene, 10 mmol-15 mmol electron donor of 3,6-dimethoxy-9,9-dimethyl acridine, 0-1 mmol palladium acetate, 1 mmol-2 mmol tri-tert-butylphosphine tetrafluoroborate, and 10 mmol-15 mmol sodium t-butoxide (NaOt-Bu). A molar ratio of the electron acceptor to the electron donor is 1:1 to 1:2.

In the present embodiment, 1.92 g (5 mmol) of the electron acceptor 4,8-dibromo-2,3,6,7-tetracyanonaphthalene, 2.2 g (8 mmol) of the electron donor of 3,6-dimethoxy-9,9-dimethyl acridine, a catalyst of 90 mg (0.4 mmol) of palladium acetate, and 0.34 g (1.2 mmol) of tri-tert-butylphosphine tetrafluoroborate are placed in a 100 mL two-necked flask, and 1.16 g (12 mmol) of sodium t-butoxide (NaOt-Bu) is added into the 100 mL two-necked flask in the glove box, the reaction liquid is obtained. Because sodium t-butoxide (NaOt-Bu) reacts easily with water to release hydrogen, it is very dangerous. Therefore, it is stored in glove box under an argon atmosphere, and it is also used under the argon atmosphere.

In a target compound synthesis step, reaction conditions of the reaction solution are provided. 30 mL to 50 mL of water and deoxygenated toluene are added into the glove box to thoroughly react at a temperature of 100° C. to 200° C. to obtain a mixed solution. The mixed solution has a target compound formed by the reaction.

In an extraction step, the mixed solution is cooled to a room temperature and poured into a 30 mL to 80 mL ice-water mixture. The target compound in the mixed solution is extracted multiple times with the dichloromethane to extract the target compound from the mixed solution.

In a target compound purification treatment step, an organic phase is combined, and the target compound is initially purified by silica gel column chromatography using a developing solvent to obtain a primary purified product. In the silica gel column chromatography method, a volume ratio of the dichloromethane to n-hexane is 1:1. The n-hexane is the solvent in the column chromatography step, and the target compound is isolated and purified to obtain a deep red powder of 1.41 g in a yield of 37%, and the deep red powder is further purified by a recrystallization method to obtain 1.2 g of the second target compound.

Results of a nuclear magnetic resonance spectrum and a carbon spectrum are: $^1$H NMR (300 MHz, $CD_2Cl_2$, δ): 8.34 (s, 2H), 7.23-7.17 (m, 4H), 6.83 (s, 4H), 6.69 (d, J=6.9 Hz, 4H), 3.70(s, 12H), 1.69(s, 12H).

A result of mass spectral is: MS (El) m/z: [M]$^+$ calcd for $C_{48}H_{38}N_6O_4$, 762.30; found, 762.07.

A result of elemental analysis is: Anal. Calcd for $C_{48}H_{38}N_6O_4$: C 75.57, H 5.02, N 11.02; found: C 75.48, H 4.93, N 10.82.

The deep-red light thermally activated delayed fluorescent material reduces a lowest singlet-triplet state energy level difference of a target molecule and a near-infrared light emission through a clever molecular design, so that the target molecule has a fast reverse intersystem crossing constant (the constant value ranges from $1 \times 10^4$/s to $1 \times 10^7$/s). The synthesizing method of the deep-red light thermally activated delayed fluorescent material synthesizes a series of deep-red light thermally activated delayed fluorescent materials with remarkable thermal activation delayed fluorescence characteristics through different coordination of functional groups, which has a high synthesis percentage. Among the synthesizing products, the thermally activated delayed fluorescent material has a high proportion in the entire synthesized products, and its photoluminescence quantum yield is high.

Characteristic parameters of the third target compound are shown in Table 5 below.

Table 5 shows the measured parameters such as the lowest singlet state (S1) and the lowest triplet state energy level (T1) of the third target compound:

| Compound | PL Peak (nm) | $S_1$ (eV) | $T_1$ (eV) | $\Box E_{ST}$ (eV) | HOMO (eV) | LUMO (eV) |
|---|---|---|---|---|---|---|
| Third target compound | 680 | 1.83 | 1.77 | 0.06 | −5.09 | −3.25 |

A photoluminescence spectrum of the third target compound in a toluene solution at room temperature is shown in FIG. 3.

As shown in FIG. 4, the present embodiment further provides an electroluminescent device comprising a substrate layer 1; a hole transporting and injecting layer 2 disposed on the upper surface of the substrate layer 1; a luminescent layer 3 disposed on an upper surface of the hole transporting and injecting layer 2; an electron transporting layer 4 disposed on an upper surface of the luminescent layer 3; and a cathode layer 5 disposed on an upper surface of the electron transporting layer 4, wherein a material of the luminescent layer 3 is a deep-red light thermally activated delayed fluorescent material, i.e., the third target compound.

A 50 nm poly 3,4-ethylenedioxythiophene: polystyrene sulfonate (PEDOT:PSS) is spin-coated on a cleaned substrate layer 1 to obtain a hole transporting and injecting layer 2. A material of the substrate layer 1 is glass and conductive glass (ITO). A 40 nm deep-red light thermally activated delayed material is spin-coated on the hole transporting and injecting layer 2 to obtain a luminescent layer 3. A layer of 40 nm of 1,3,5-tris(3-(3-pyridyl)phenyl)benzene (Tm3PyPB) is evaporated on the luminescent layer 3 under high vacuum to obtain an electron transporting layer 4. Further, under high vacuum conditions, a layer of 1 nm lithium fluoride and 100 nm aluminum are evaporated on the electron transporting layer 4 to obtain a cathode layer 5, thereby finally forming a first electroluminescent device.

A current-brightness-voltage characteristic of the device is performed by a Keithley source measurement system (Keithley 2400 Sourcemeter, Keithley 2000 Currentmeter) with a calibrated silicon photodiode. An electroluminescence spectrum is measured by a French JY company SPEX CCD3000 spectrometer. All measurements are done at room temperature in an atmosphere.

A performance data of the third electroluminescent device is shown in Table 6 below.

Table 6 shows measured parameters such as a highest brightness and a highest current efficiency of the second electroluminescent device:

| Electroluminescent device | highest brightness (cd/m$^2$) | highest current efficiency (cd/A) | CIEx | Maximum external quantum efficiency (%) |
|---|---|---|---|---|
| Third electroluminescent device | 1.83 | 1.77 | 0.06 | −5.09 |

The electroluminescent device fabricated by deep-red light thermally activated delayed fluorescent material has a relatively high luminous efficiency and brightness, a high production efficiency and a long service life.

When a molar ratio of the electron acceptor to the electron donor is from 1:1 to 1:2, the synthesized molecular structure is a D-A molecular structure. The molecular structure is as follows:

The thermally activated delayed fluorescent material of the D-A molecular structure has a high proportion in the entire synthesized product, and its photoluminescence quantum yield is high but the performance is lower than a D-A-D structure. The D-A-D structure reduces the lowest singlet-triplet energy level difference of the target molecule and a near-infrared light emission, so that the target molecule has a fast reverse intersystem crossing constant (the constant value ranges from $1 \times 10^4$/s to $1 \times 10^7$/s) and a high photoluminescence quantum yield.

The description above is merely preferred embodiments of the present disclosure. It is noted that, for one skilled in the art, many changes and modifications to the described embodiment can be carried out without departing from the principles of the disclosure and these changes and modifications should also be considered as protection scope of the present disclosure.

The invention claimed is:

1. A deep-red light thermally activated delayed fluorescent material, which is a target compound reacted and synthesized by an electron donor and an electron acceptor, wherein the target compound is a D-A molecular structure or a D-A-D molecular structure, the D in the molecular structure is the electron donor, the A is the electron acceptor, the electron acceptor is a planar electron acceptor with an ultra-low triplet state energy level, and a triplet state energy level of the target compound ranges from 1.0 to 2.0 eV, wherein the electron acceptor is 4,8-dibromo-2,3,6,7,-tetracyanonaphthalene, and the electron donor includes at least one of phenoxazine, phenothiazine, and 3,6-dimethoxy-9,9-dimethyl acridine.

2. The deep-red light thermally activated delayed fluorescent material according to claim 1,
wherein the D-A molecular structure of the deep-red light thermally activated delayed fluorescent material is:

wherein the D-A-D molecular structure of the deep-red light thermally activated delayed fluorescent material is:

3. An electroluminescent device, comprising:
a substrate layer;
a hole transporting and injecting layer disposed on a side surface of the substrate layer;
a luminescent layer disposed on a side surface of the hole transporting and injecting layer away from the substrate layer;
an electron transporting layer disposed on a side surface of the luminescent layer away from the hole transporting and injecting layer; and
a cathode layer disposed on a side surface of the electron transporting layer away from the luminescent layer;
wherein a material of the luminescent layer is a deep-red light thermally activated delayed fluorescent material according to claim 1.

* * * * *